(12) United States Patent
Hochi et al.

(10) Patent No.: US 10,119,000 B2
(45) Date of Patent: Nov. 6, 2018

(54) LAMINATE FILM USING POLYLACTIC ACID-BASED RESIN

(71) Applicants: TORAY INDUSTRIES, INC., Tokyo (JP); NANOTHETA CO, LTD., Tokyo (JP)

(72) Inventors: Motonori Hochi, Otsu (JP); Yuki Goto, Otsu (JP); Katsuhiro Minomo, Otsu (JP); Naomi Tamimiya, Otsu (JP)

(73) Assignees: TORAY INDUSTRIES, INC., Tokyo (JP); NANOTHETA CO, LTD., Tokyo (JP)

( * ) Notice: Subject to any disclaimer, the term of this patent is extended or adjusted under 35 U.S.C. 154(b) by 371 days.

(21) Appl. No.: 14/772,542

(22) PCT Filed: Mar. 6, 2014

(86) PCT No.: PCT/JP2014/055711
§ 371 (c)(1),
(2) Date: Sep. 3, 2015

(87) PCT Pub. No.: WO2014/141983
PCT Pub. Date: Sep. 18, 2014

(65) Prior Publication Data
US 2016/0002422 A1  Jan. 7, 2016

(30) Foreign Application Priority Data
Mar. 15, 2013  (JP) .................................. 2013-053191

(51) Int. Cl.
| | | |
|---|---|---|
| *C08J 5/18* | (2006.01) | |
| *A61L 15/50* | (2006.01) | |
| *B32B 27/36* | (2006.01) | |
| *A61L 15/22* | (2006.01) | |
| *B32B 27/08* | (2006.01) | |
| *B32B 27/30* | (2006.01) | |
| *B32B 3/30* | (2006.01) | |
| *B32B 7/02* | (2006.01) | |
| *A61L 15/64* | (2006.01) | |
| *A61L 15/24* | (2006.01) | |
| *A61L 15/26* | (2006.01) | |
| *A61L 15/28* | (2006.01) | |

(52) U.S. Cl.
CPC .............. *C08J 5/18* (2013.01); *A61L 15/225* (2013.01); *A61L 15/24* (2013.01); *A61L 15/26* (2013.01); *A61L 15/28* (2013.01); *A61L 15/50* (2013.01); *A61L 15/64* (2013.01); *B32B 3/30* (2013.01); *B32B 7/02* (2013.01); *B32B 27/08* (2013.01); *B32B 27/306* (2013.01); *B32B 27/36* (2013.01); *B32B 2307/538* (2013.01); *B32B 2556/00* (2013.01); *C08J 2305/00* (2013.01); *C08J 2329/04* (2013.01); *C08J 2367/00* (2013.01); *C08J 2367/04* (2013.01); *C08J 2405/00* (2013.01); *C08J 2429/04* (2013.01); *C08J 2467/00* (2013.01); *C08J 2467/04* (2013.01)

(58) Field of Classification Search
CPC ....... B32B 27/36; B32B 27/08; B32B 27/306; A61L 15/20–15/28; A61L 15/42; A61L 15/58–15/585; C08L 67/04; C08L 29/04; C08J 5/18
See application file for complete search history.

(56) References Cited

U.S. PATENT DOCUMENTS

| | | | | |
|---|---|---|---|---|
| 3,784,390 A | * | 1/1974 | Hijiya | A61K 9/4816 106/144.72 |
| 6,946,182 B1 | * | 9/2005 | Allgeuer | B29C 43/222 264/134 |
| 2003/0118850 A1 | * | 6/2003 | McCormack | B32B 7/02 428/480 |
| 2007/0237812 A1 | * | 10/2007 | Patel | A61L 15/46 424/446 |
| 2009/0136714 A1 | * | 5/2009 | Itou | C08J 5/18 428/152 |
| 2011/0236635 A1 | * | 9/2011 | Shimizu | B29C 55/023 428/141 |
| 2012/0078155 A1 | * | 3/2012 | Bowman | A61L 15/26 602/54 |
| 2012/0301515 A1 | | 11/2012 | Tani et al. | |

FOREIGN PATENT DOCUMENTS

| | | | | |
|---|---|---|---|---|
| JP | 1-229805 A | | 9/1989 | |
| JP | 2000-189509 A | | 7/2000 | |
| JP | 2005008733 A | * | 1/2005 | |
| JP | 2006-6448 A | | 1/2006 | |
| JP | 2006006448 A | * | 1/2006 | |
| JP | 2008-109979 A | | 5/2008 | |
| WO | WO 2011/046226 A1 | | 4/2011 | |
| WO | WO-2011046226 A1 | * | 4/2011 | ............... C08J 3/05 |
| WO | WO 2011/081162 A1 | | 7/2011 | |

OTHER PUBLICATIONS

Machine translation of JP2005008733. Retrieved Oct. 15, 2017.*

(Continued)

*Primary Examiner* — Prashant J Khatri
(74) *Attorney, Agent, or Firm* — Birch, Stewart, Kolasch & Birch, LLP

(57) ABSTRACT

Our invention is a laminate film comprising a water-soluble resin layer and a polylactic acid-based resin layer laminated on at least one side of a substrate film, the water-soluble resin layer has a thickness of 0.1 to 15 μm, the polylactic acid-based resin layer has a thickness of 10 to 500 nm. Such a configuration provides a laminate film of which the water-soluble resin layer and the polylactic acid-based resin layer are easily separated from the substrate film and which is excellent in coating ability, adherence and followability to a soft and curved adherend, as well as compatibility to skin and organs such as viscera, so as to be suitable for wound dressing, adhesion prevention material and a skin external agent such as skin-care product.

5 Claims, No Drawings

(56) References Cited

OTHER PUBLICATIONS

"General Information of 'Kuraray Poval'". Kuraray Co., Ltd. http://www.poval.jp/english/poval/g_info/gi_05.html. Copyright 2004.*
Machine translation of WO2011046226. Retrieved Jul. 31, 2018.*
Machine translation of JP2006006448. Retrieved Jul. 31, 2018.*
International Search Report, issued in PCT/JP2014/055711, dated Jun. 10, 2014.
Okamura et al. "Fragmentation of Poly(lactic acid) Nanosheets and Patchwork Treatment for Burn Wounds", Advanced Materials, 2013, 25, 545-551.
Written Opinion of the International Searching Authority, issued in PCT/JP2014/055711, dated Jun. 10, 2014.

* cited by examiner

LAMINATE FILM USING POLYLACTIC ACID-BASED RESIN

TECHNICAL FIELD OF THE INVENTION

The present invention relates to a laminate film using a polylactic acid-based resin suitable for medical use such as wound dressing membrane and adhesion prevention membrane.

BACKGROUND ART OF THE INVENTION

Surgical operations typified by abdominal surgery, orthopedic surgery, neurosurgery and the like may have a problem of adhesion between organs, as a postoperative complication. It means that when normal tissues damaged with drying and oxidation in the surgery are sutured, organ tissues that should not join may be joined together to cause adhesion phenomenon in a process of self-cure of wound. Surgery operations are supposed to accompany the adhesion in a high rate, so that complications may cause pains or serious conditions such as intestinal obstruction (ileus) and infertility.

Once the adhesion occurs, medication treatment may not be effective. The adhesion may cause intestinal obstruction after some years from the surgery. The adhesion prevention is very important in a surgery operation because the adhesion can only be cured by the synechiotomy to peel adhered area by additional surgery operation.

For a postoperative treatment to prevent tissue adhesion and delayed cure, exposed organ tissues are conventionally covered with gauze immersed in saline to prevent drying and oxidation. However, soft and complicated organs may not be fully covered with gauze. Furthermore, a doctor may be disturbed with gauze in a surgery or forget to get rid of gauze from the body where much gauze is used.

For such reasons, organ tissues can be physically separated as using an adhesion prevention membrane made of material such as silicone, "Teflon" (registered trademark), polyurethane and oxycellulose, which perform adhesion prevention or delayed cure prevention. But these non-absorbable materials which tend to stay on a biotissue may delay the tissue restoration and cause infection or inflammation.

To solve such problems, Patent documents 1 and 2 disclose adhesion prevention materials made with gelatin or collagen which is expected to be bioabsorbable. However, it is difficult to remove antigenic telopeptide from the material made with gelatin or collagen. Also, they say such a material should not be used in the body in view of risk of infection such as prion contamination derived from animals. Further, it is thought that a cross-linker added to control the strength or degradability is often undesirable for in vivo use.

On the other hand, natural polymers having good affinity to skin may have poor strength. Therefore the natural polymers have to be reinforced, by cross-linking with cross-linker, by reinforcing with reinforcing material, by coating with gauze, or the like. The reinforcing material may not be practical in view of the complicated structure.

Patent document 3 discloses an adhesion prevention material made with polysaccharide such as trehalose having no risk of infection. However, such a material made with polysaccharides may not have sufficient strength and therefore may not be sutured because of poor strength in suturing. Even if it can be sutured successfully, it is difficult to maintain the sutured condition for a certain time.

Patent document 4 discloses an adhesion prevention material made with hyaluronic acid. But such a material has a poor adhesiveness to organs and tends to slide on the organ to cause adhesion. Therefore it may not have a sufficient ability. Further, it may be manufactured at a higher manufacturing cost because mass production is difficult. There are some ways to make the adhesion prevention membrane firmly adhere to organs or the like by using blood products or chemical substances. But such a membrane has to be handled carefully with a good hygiene and safety.

Although thus there are many reports about materials for adhesion prevention of tissues, there is no material that is sufficiently qualified as an adhesion prevention material. Accordingly, they require a material that can prevent an adhesion as maintaining the strength until the tissue is restored.

PRIOR ART DOCUMENTS

Patent Documents

Patent document 1: JP2004-065780-A
Patent document 2: JP2001-192337-A
Patent document 3: JP2003-153999-A
Patent document 4: WO2005/094915

SUMMARY OF THE INVENTION

Problems to be Solved by the Invention

Focused on the background technics of the prior arts, our invention is to provide a laminate film that is excellent in biocompatible, can easily be handled, and is economically excellent.

Means for Solving the Problems

Our invention employs the following compositions to solve the problem described above.
(1) A laminate film comprising a water-soluble resin layer and a polylactic acid-based resin layer laminated on at least one side of a substrate film, characterized in that the water-soluble resin layer has a thickness of 0.1 to 15 μm, the polylactic acid-based resin layer has a thickness of 10 to 500 nm.
(2) The laminate film according to (1), wherein the water-soluble resin layer contains a polyvinyl alcohol.
(3) The laminated film according to (2), wherein the polyvinyl alcohol has a saponification degree of 85 to 98.5 mol %.
(4) The laminate film according to (1), wherein the polylactic acid-based resin layer contains a polylactic acid-based resin including a poly-D-lactic acid of 4 to 13 mol %.
(5) The laminate film according to (1), wherein the water-soluble resin layer contains a pullulan.
(6) The laminate film according to (1), wherein the substrate film has a center-line average surface roughness (SRa) of 3 to 50 nm and a ten-point average surface roughness (SRz) of 50 to 1000 nm.

Effect According to the Invention

Our invention provides a laminate film comprising a water-soluble resin layer and a polylactic acid-based resin layer laminated on at least one side of a substrate film, so that the water-soluble resin layer and the polylactic acid-based resin layer are easily separated from the substrate film.

The laminate film comprising the water-soluble resin layer and the polylactic acid-based resin layer is excellent in covering ability, adhesion and followability to a soft and curved adherend, as well as compatibility to skin and organs such as viscera, so as to be suitable for wound dressing, adhesion prevention material and a skin external agent such as skin-care product.

Further, the laminate film comprising the polylactic acid-based resin layer and the water-soluble resin layer can be mass-produced cheaply and therefore is economical.

Furthermore, because the adhesion side of the polylactic acid-based resin layer is transparent and less-visible on a scar, the laminate film can be used as an adhesive plaster to be pasted on skins, other than the surgical use.

Besides, the polylactic acid-based resin layer can be used as a substrate supporting and controlling to release various drugs, so that a drug delivery system is provided.

EMBODIMENTS FOR CARRYING OUT THE INVENTION

Hereinafter, our invention will be explained. In the specification, the term "film" means a two-dimensional structure such as sheet, plate and discontinuous membrane.

<Substrate Film>

Our invention employs substrate films made of polymer material. The substrate film may be made of polyolefin such as polyethylene and polypropylene, polyester such as polyethylene terephthalate, polybutylene terephthalate and polyethylene-2,6-naphthalate, polyamide such as nylon 6 and nylon 12, polyvinyl chloride, ethylene-vinyl acetate copolymer or saponificate thereof, polystyrene, polycarbonate, polysulfone, polyphenylene oxide, polyphenylene sulfide, aromatic polyamide, polyimide, polyamide-imide, cellulose, cellulose acetate, polyvinylidene chloride, polyacrylonitrile, polyvinyl alcohol, copolymer thereof or the like. From viewpoints of ensuring adhesion between water-soluble resin layer and polylactic acid-based resin layer as well as uniform thickness of laminate film, it is preferable that the substrate film is made of polyester such as polyethylene terephthalate, or made of polyolefin such as polyethylene and polypropylene. The polyester such as polyethylene terephthalate is particularly preferable because of higher wet tension on surface.

It is more preferable that a surface treatment, such as corona discharge processing, flame processing, plasma processing and ultraviolet irradiation processing, is performed on the substrate film before forming a coat layer of the water-soluble resin layer and the polylactic acid-based resin layer.

It is preferable that the substrate film, which may be unstretched film, uniaxially-oriented film or biaxially-oriented film, is a biaxially oriented film, from viewpoints of dimension stability and mechanical property.

It is possible that the substrate film contains various additives. For example, it may contain antioxidant, weathering agent, heat stabilizer, lubricant, crystalline nucleus agent, ultraviolet ray absorbing agent, coloring agent or the like. It may contain inorganic or organic particles to the extent that the surface smoothness does not deteriorate significantly. For example, it may contain talc, kaolinite, calcium carbonate, titanium oxide, silicon oxide, calcium fluoride, lithium fluoride, alumina, barium sulfate, zirconia, mica, calcium phosphate, cross-linked polystyrene-based particles or the like.

It is preferable that the particles have an average particle diameter from 0.001 to 10 μm, preferably from 0.003 to 5 μm. The average particle diameter is a number average value obtained from transmission electron microscope photographs magnified from 10,000 to 100,000 times.

It is preferable that the substrate film is transparent. It is preferable that the substrate film has a total light transmittance of 40% or more. It is preferably 60% or more, while the upper limit may be almost 100%. It is preferable that the substrate film has a haze of 20% or less, preferably 15% or less. The haze of more than 20% might make it difficult for an optical detector to detect impurities included in the laminated water-soluble resin layer and polylactic acid-based resin layer. The lower limit of haze is not limited and may be almost 0%.

It is preferable that the substrate film has a thickness of 2 to 1000 μm. It is preferable that it has a thickness of 10 to 500 μm from a viewpoint of economy.

It is preferable that the substrate film has a center-line average surface roughness (SRa) of 3 to 50 nm. It is preferable that it has an SRa of 5 to 40 nm, more preferably 5 to 20 nm. The center-line average surface roughness (SRa) of less than 3 nm might make the surface excessively smooth to cause great friction, so that the film may be less conveyable and have wrinkles when rolled up. The center-line average surface roughness (SRa) of more than 50 nm might have surface unevenness causing defects such as uncoated area and pinholes when performing coating.

It is preferable that the substrate film has a ten-point average surface roughness (SRz) of 50 to 1000 nm. It is preferable that it has an SRz of 100 to 800 nm, more preferably 100 to 600 nm, particularly preferably 100 to 400 nm. The ten-point average surface roughness (SRz) of less than 50 nm might make the surface excessively smooth to cause great friction, so that the film may be less conveyable and have wrinkles when rolled up. The ten-point average surface roughness (SRz) of more than 1,000 nm might have surface unevenness causing defects such as uncoated area and pinholes when performing coating.

The substrate film surface prescribed with a three-dimensional roughness such as the above-described SRa and SRz means a surface on which the polylactic acid-based resin layer and the water-soluble resin layer are laminated.

The three-dimensional roughness of the substrate film is a value of the center-line average surface roughness (SRa) or the ten-point average surface roughness (SRz) determined according to JIS B0601:1996 with surface profiles obtained by scanning target area S [0.4 mm$^2$ (1 mm×0.4 mm)] with a three-dimensional contact probe profilometer having probe curvature radius of 2 μm, while the scanning is performed 81 times with 5 μm span orthogonal to the scanning direction under a condition of cut-off level of 0.25 mm and scanning length of 1 mm.

It is possible to form an additional layer made of bioabsorbable material such as gelatin, collagen, hyaluronic acid, chitosan and synthetic polypeptide on at least one side of the polylactic acid-based resin layer as far as the effect of our invention is not spoiled.

To improve adhesion of the substrate film to the water-soluble resin layer and the polylactic acid-based resin layer, it is possible that a coat layer is provided on an anchor layer formed on the substrate film with anchoring agent such as urethane resin, epoxy resin and polyethylenimine. It is preferable that the anchor layer has a thickness of 0.1 to 5.0 μm.

<Polylactic Acid-Based Resin Layer>

It is preferable that the polylactic acid-based resin layer is made of a polylactic acid-based resin containing poly-L-lactic acid (L body) and/or poly-D-lactic acid (D body) as primary component. The "primary component" means a component containing 70 mol % to 100 mol % of lactic acid-derived components among 100 mol % of all monomer components constituting the polylactic acid-based resin. It is preferable that the primary component is a homopolymer of lactic acid-based resin consisting substantially of poly-L-lactic acid and/or poly-D-lactic acid only.

It is preferable that the polylactic acid-based resin contains the poly-D-lactic acid of 4 to 13 mol %, preferably 6 to 13 mol %. The poly-D-lactic acid of less than 4 mol % might decrease the solubility in organic solvents and fail to provide a coating agent. The poly-D-lactic acid of more than 13 mol % might deteriorate the biocompatibility.

It is preferable that the polylactic acid-based resin is crystalline. The term "crystalline" means characteristics observed as heat of fusion for crystal that is derived from polylactic acid component when the polylactic acid-based resin is heated to fully crystalize and then is subject to differential scanning calorimetry (DSC) at an appropriate temperature condition. The homopolymer of lactic acid-based resin usually has higher melting point and crystallinity when the optical purity is higher. The melting point and crystallinity of the polylactic acid-based resin are affected by the molecular weight and catalyst used at polymerization. The homopolymer of lactic acid-based resin having optical purity of 98% or more has melting point around 170° C. and a higher crystallinity. The lower the optical purity becomes, the lower the melting point and the crystallinity become. For example, a homopolymer of lactic acid-based resin having optical purity of 88% has melting point around 145° C. while a homopolymer of lactic acid-based resin has melting point around 120° C. A homopolymer of lactic acid-based resin having an optical purity of less than 70% would not have a definite melting point and is noncrystalline.

The polylactic acid-based resin should usually have a weight average molecular weight of 50,000 or more. The weight average molecular weight is preferably 80,000 to 400,000, preferably 100,000 to 300,000. The term "weight average molecular weight" means a molecular weight calculated by the polymethylmethacrylate (PMMA) conversion method from a measurement result with chloroform solvent in gel permeation chromatography (GPC). 500,000 or more of the weight average molecular weight of the polylactic acid-based resin can make the polylactic acid-based resin layer, as well as a laminate film having the water-soluble resin layer and polylactic acid-based resin layer, have an excellent mechanical property.

To improve the solubility in solvents for preparing the coating agent, crystalline homopolymer of polylactic acid-based resin and amorphous homopolymer of lactic acid-based resin may be mixed to prepare the polylactic acid-based resin. The amorphous homopolymer of lactic acid-based resin should be mixed in such a proportion that the effect of our invention isn't spoiled. To give a higher heat resistance to the laminate film having the water-soluble resin layer and polylactic acid-based resin layer, it is preferable that at least one of the polylactic acid-based resin has an optical purity of 95% or more.

The polylactic acid-based resin may be a copolymerized polylactic acid-based resin made by copolymerizing another monomer component having ester formation ability with L-lactic acid and D-lactic acid. The monomer component to be copolymerized may be a hydroxy carboxylic acid such as glycolic acid, 3-hydroxybutyric acid, 4-hydroxybutyric acid, 4-hydroxy valeric acid and 6-hydroxy caproic acid, a compound of which molecule contains a plurality of hydroxyl groups, such as ethylene glycol, propylene glycol, butanediol, neopentylglycol, polyethylene glycol, glycerin, pentaerythritol and derivative thereof, another compound of which molecule contains a plurality of carboxylic acid groups, such as succinic acid, adipic acid, sebacic acid, fumaric acid, terephthalic acid, isophthalic acid, 2,6-naphthalenedicarboxylic acid, 5-sodium sulfoisophthalic acid, 5-tetrabutyl phosphonium sulfoisophthalic acid and derivative thereof, or the like. It is preferable that the above-described copolymerizing component is biodegradable depending on a use. It is preferable that the polylactic acid-based resin contains the copolymerizing component of more than 0 mol % and less than 30 mol % among total 100 mol % of monomer components.

The polylactic acid-based resin may be produced by a polymerization such as polymerization directly from lactic acid and ring-opening polymerization through lactide, to be described later.

From viewpoints of giving durability (long-term storage stability) and suppressing strength degradation from hydrolysis, it is preferable that the polylactic acid-based resin has a carboxyl terminal concentration of 30 equivalent/$10^3$ kg or less. It is preferably 20 equivalent/$10^3$ kg or less, preferably 10 equivalent/$10^3$ kg or less. The carboxyl terminal concentration of 30 equivalent/$10^3$ kg or less can provide a good practical durability because such a low carboxyl terminal concentration has little autocatalytic function to hydrolysis. The carboxyl terminal concentration in the polylactic acid-based resin is not limited in particular and may be almost 0 equivalent.

The carboxyl terminal concentration in the polylactic acid-based resin can be controlled to 30 equivalent/$10^3$ kg or less by a method, such as designing catalyst or heat history in synthesizing the polylactic acid-based resin, decreasing heat history by lowering the processing temperature or shortening the heating time in forming films, and blocking the carboxyl terminal with a reactive compound.

In the method of blocking the carboxyl terminal with a reactive compound, it is preferable that the carboxyl terminal is fully blocked although it may be partially blocked. The reactive compound may be condensation reaction-type compound such as aliphatic alcohol and amide compound, addition reaction-type compound such as carbodiimide compound, epoxy compound and oxazoline compound, or the like. It is preferable that the reactive compound is the addition reaction-type compound so that byproduct is hardly produced in reacting. From a viewpoint of reaction efficiency, it is preferably the carbodiimide compound.

To improve mechanical strength, the polylactic acid-based resin layer may contain an impact modifier of 2 mass % or more and 20 mass % or less among total 100 mass % of a whole laminate film. The content is preferably 2.5 mass % or more, and 15 mass % or less. The more the impact modifier is contained the more the impact resistance improves, although impact modifier of more than 20 mass % could not greatly improve the mechanical strength.

It is preferable that the impact modifier for improving the impact resistance is an aliphatic polyester or aliphatic-aromatic polyester other than the polylactic acid-based resin because its desirable dispersibility in the polylactic acid-based resin can make a better effect.

The aliphatic polyester or aliphatic-aromatic polyester other than the polylactic acid-based resin may be polyglycolic acid, poly-3-hydroxybutyric acid, poly-4-hydroxybutyric acid, poly-4-hydroxy valeric acid, poly-3-hydroxy hexanoic acid, polycaprolactone, polyethylene adipate, polyethylene succinate, polybutylene succinate, polybutylene succinate adipate or the like.

To improve the mechanical strength and maintain the biodegradability, it is preferable that the aliphatic polyester other than the polylactic acid-based resin is a polybutylene succinate-based resin. It is more preferable to employ the polybutylene succinate or polybutylene succinate adipate that are compatible to the polylactic acid-based resin and advantageous for improving the mechanical strength.

It is preferable that the polybutylene succinate-based resin has a weight average molecular weight of 100,000 to 300,000. The polybutylene succinate-based resin can be prepared by polycondensation of 1,4-butanediol and succinic acid.

The polylactic acid-based resin can be prepared by the following method. For raw materials, the hydroxy carboxylic acid other than the lactic acid components can be employed together with a lactic acid component of L-lactic acid or D-lactic acid. It is possible to employ a cyclic ester intermediate, such as lactide and glycolide, of the hydroxy carboxylic acid as a raw material. A dicarbon acid or glycol may be employed.

The polylactic acid-based resin can be prepared by direct dehydration condensation with the raw material, or alternatively by ring-opening polymerization of the cyclic ester intermediate. In the direct dehydration condensation, a lactic acid, with or without hydroxy carboxylic acid, is subject to azeotrope dehydration preferably in the presence of an organic solvent such as phenyl ether-based solvent, and then water is preferably removed from a solvent distilled through azeotropy to make the solvent substantially anhydrous to be polymerized in the reaction system to obtain polymers having a high molecular weight.

It is known that the cyclic ester intermediate such as lactide can be subject to ring-opening polymerization with catalyst such as tin octylate under reduced pressure to obtain a polymer having a high molecular weight. To obtain a polymer having less content of lactide, it is possible that conditions of removing water and low-molecular compounds are adjusted in organic solvent at the time of heating to reflux. Alternatively, catalyst may be deactivated to control a depolymerization after the polymerization reaction, or the produced polymer may be heat-treated.

From a viewpoint of shape followability to adherend, the polylactic acid-based resin layer should usually have a thickness of 10 to 500 nm, preferably 10 to 100 nm. The thickness of less than 10 nm might not be able to preserve a shape, while the thickness of more than 500 nm might have wrinkles when pasted on the adherend.

From a viewpoint of adherence on the adherend, the polylactic acid-based resin layer should usually have a thickness of 10 to 500 nm, preferably 10 to 300 nm. It is more preferably 50 to 250 nm, particularly preferably 160 to 250 nm, and is most preferably 160 to 200 nm. The thickness of less than 10 nm or more than 500 nm might deteriorate the adherence on the adherend.

It is possible that various additives of 30 mass % or less are contained in total 100 mass % of a whole laminate film as far as the effect of our invention is not spoiled. The various additives may be antioxidant, weathering agent, heat stabilizer, lubricant, crystalline nucleus agent, ultraviolet absorbing agent, coloring agent or the like. Such additives may be contained by almost 0 mass % in total 100 mass % of the whole laminate film. It is possible that inorganic or organic particles of 20 mass % or less are contained in total 100 mass % of the whole laminate film mass, as far as transparency is maintained. The particle may be calcium carbonate, titanium oxide, silicon oxide, calcium fluoride, lithium fluoride, alumina, barium sulfate, zirconia, calcium phosphate, cross-linked polystyrene-based particle, metal nanoparticle or the like. The inorganic or organic particle may be contained by almost 0 mass % in total 100 mass % of the whole laminate film.

<Water-Soluble Resin Layer>

The water-soluble resin constituting the water-soluble resin layer may be a macromolecule material capable of dissolving in water, warm water, normal saline solution and glucose solution. For example, the water-soluble resin may preferably be a polysaccharide such as polyvinyl alcohol or copolymer thereof, dextran, agarose, pullulan, chitosan, mannan, carrageenan, alginic acid, starch (e.g. oxidation starch, etherification starch, dextrin), amylose, amylopectin, pectin, lentinan, hyaluronic acid, hiran, and cellulose derivative (e.g. methylcellulose, ethyl cellulose, carboxymethylcellulose, carboxy ethyl cellulose, hydroxyethyl cellulose, hydroxypropyl cellulose), a polypeptide such as gelatin, collagen, elastin, albumin, hemoglobin, transferrin, globulin, fibrin, fibrinogen and keratin sulfuric acid, a copolyester having a polar group such as polyvinylpyrrolidone and sulfoisophthalic acid, a vinyl-based polymer such as polyhydroxyethyl methacrylate or copolymer thereof, acryl-based macromolecule, urethane-based macromolecule, ether-based macromolecule or the like. It is also preferable to employ a polymer made by modifying such various polymers with a functional group such as carboxyl group, amino group and methylol group. From viewpoints of production cost, availability and hygiene, it is preferable to employ the polyvinyl alcohol or copolymer thereof, or pullulan.

The polyvinyl alcohol is a saponificate of polyvinyl acetate, of which saponification degree is preferably 85 to 98.5 mol %, preferably 85 to 90 mol %. The saponification degree of more than 98.5 mol % might deteriorate the solubility of the water-soluble resin layer of polyvinyl alcohol to water.

It is preferable that the polyvinyl alcohol copolymer has a vinyl alcohol unit of 80 to 98 mol %, preferably 85 to 98 mol %. The term "saponification degree" means a proportion [mol %] of vinyl alcohol unit [mol] relative to the total [mol] of the vinyl alcohol unit and a structure unit (typically a vinyl ester unit) that can be converted into the vinyl alcohol unit through saponification. The saponification degree can be determined according to JIS K6726: 1994.

The pullulan is a water-soluble resin polymer of a kind of polysaccharide consisting of maltotriose units, in which three glucose units in maltotriose are connected by an α-1,4 glycosidic bond, whereas consecutive maltotriose units are connected to each other by an α-1,6 glycosidic bond.

The pullulan is usually advantageous from viewpoints of availability and price. The pullulan is advantageously produced in medium containing starch resolvent in which the yeast fungus such as *Aureobasidium* is cultivated. For example, pullulan products ("pullulan PI-20" and "pullulan PF-20") made by Hayashibara Co., Ltd. are suitably employed. Other pullulan products may be employed within the purpose of our invention. It is possible that the repeating unit is a maltotriose derivative esterified by any substitution degree as needed.

It is usually preferable that the pullulan has a weight average molecular weight of 5,000 to 1,000,000 Daltons. It is preferably 10,000 to 1,000,000 Daltons, more preferably 50,000 to 500,000 Daltons. The weight average molecular weight and molecular weight distribution of the pullulan can be selected to design the water-soluble resin layer having a desirable collapse speed. Although depending on other components, it may be difficult to form a sheet-like film with the pullulan having a weight average molecular weight of less than 5,000 Daltons. The molecular weight of more than 1,000,000 Daltons might decrease the dissolution speed in aqueous solvent excessively.

It is preferable that the water-soluble resin constituting the water-soluble resin layer has an average polymerization degree of 100 to 5,000. It is preferably 200 to 2,500, and is more preferably 400 to 1,800. The term "average polymerization degree" means a number average polymerization degree. The average polymerization degree is in this range can make a uniform coat layer having a high mechanical strength as well as excellent re-solubility to water solution. In the specification, the average polymerization degree of polyvinyl alcohol is determined according to JIS K6726: 1994.

It is possible that two or more kinds of water-soluble polymer having different average polymerization degrees are mixed. By mixing them, the coat layer can have a high mechanical strength and re-solubility, as well as good adhesion to the substrate film and the polylactic acid-based resin. It is preferable that a low-polymerization water-soluble polymer having an average polymerization degree of 100 to 800 and a high-polymerization water-soluble polymer having an average polymerization degree of 1,000 to 2,500 are mixed. It is preferable that the low-polymerization water-soluble polymer has an average polymerization degree of 300 to 700. It is preferable that the high-polymerization water-soluble polymer has an average polymerization degree of 1,300 to 1,700.

It is possible that various additives of 30 mass % or less are contained in total 100 mass % of a whole water-soluble resin layer, as far as the effect of our invention is not spoiled. The content is not limited in particular and may be 0 mass %. The various additives may be antioxidant, weathering agent, heat stabilizer, lubricant, crystalline nucleus agent, ultraviolet absorbing agent, coloring agent or the like. It is possible that inorganic or organic particles of 20 mass % or less are contained, as far as the effect of our invention is not spoiled. The content is not limited in particular and may be 0 mass %. The particle may be calcium carbonate, titanium oxide, silicon oxide, calcium fluoride, lithium fluoride, alumina, barium sulfate, zirconia, calcium phosphate, cross-linked polystyrene-based particle, metal nanoparticle or the like.

From a viewpoint of shape followability to adherend, the water-soluble resin layer should usually have a thickness of 0.1 to 15 μm, preferably 1.0 to 15 μm. The thickness is preferably 1.0 to 10 μm, more preferably 1.0 to 5.0 μm, further preferably 1.0 to 4.0 μm, and is most preferably 2.0 to 4.0 μm. The thickness of less than 0.1 μm might make the shape difficult to be preserved. The thickness of more than 15 μm might cause wrinkles when the layer is pasted on the adherend, or make the separation from the polylactic acid-based resin difficult as it takes too much time in re-solving in water.

<Laminate Film>

From viewpoints of peeling ability, handling ability and preservation, it is preferable that the substrate film has a peeling strength of $5\times10^{-3}$ to $5,000\times10^{-3}$ [N/10 mm] to peel the polylactic acid-based resin layer or the water-soluble resin layer from the substrate film at temperature of 23±2° C. and humidity of 65±5%. It is preferably $5\times10^{-3}$ to $2,000\times10^{-3}$ [N/10 mm], more preferably $5\times10^{-3}$ to $1,000\times10^{-3}$ [N/10 mm], particularly preferably $5\times10^{-3}$ to $300\times10^{-3}$ [N/10 mm], most preferably $5\times10^{-3}$ to $100\times10^{-3}$ [N/10 mm]. The peeling strength of more than $5,000\times10^{-3}$ [N/10 mm] might cause a breakage or crack of the laminate film when the laminate film is peeled from the substrate film. The peeling strength of less than $5\times10^{-3}$ [N/10 mm] might not laminate the water-soluble resin layer or the polylactic acid-based resin layer because the polylactic acid-based resin layer or the water-soluble resin layer peels easily from the substrate when the substrate is coated with the water-soluble resin layer or the polylactic acid-based resin layer.

The laminate film may be used as a laminate film itself, or alternatively be used as being laminated on another material. Such another material can be a material generally available and may be paper, metal such as aluminum and silicon or oxide thereof, nonwoven fabric, resin film, biomembrane or the like.

The resin film may be unstretched film, biaxially-oriented film, coextruded film, coating film, vapor-deposited film, molten extruded resin or the like. The raw material of the resin film may be a polyolefin such as polyethylene and polypropylene, a polyester such as polyethylene terephthalate, polybutylene terephthalate and polyethylene-2,6-naphthalate, a polyamide such as nylon 6 and nylon 12, a polyvinyl chloride, a polyvinylidene chloride, a polyvinyl acetate or a saponificate thereof, an ethylene vinyl acetate copolymer or saponificate thereof, a polystyrene, an aromatic polyamide, an ionomer resin, a polycarbonate, a polysulfone, a polyphenylene oxide, a polyphenylene sulfide, a polyimide, a polyamide-imide, a cellulose, a cellulose acetate, a polyacrylonitrile or the like, or a copolymer thereof.

The biomembrane means a membrane surrounding various cells or organelles. The cell includes cells of various parts, organs and organization, blood cells, generative cells and the like. The organelle means a cytoplasmic formed element having a certain function and including Goldi body, mitochondria, centriole, ribosome, endoplasmic reticulum, lysosome, nuclear membrane and the like.

The lamination composition is not limited particularly and may have a print layer, adhesive layer or anchor layer between the laminate film and another material.

<Producing Method>

The laminate film and polylactic acid-based resin film can be produced by a typical producing method as follows.

[Forming Method of Coat Layer]

When the substrate film is a biaxially-oriented film of polyester such as polyethylene terephthalate or polyolefin such as polypropylene, a off-line coat method for coating after a film forming process of the biaxially-oriented film or an in-line coat method for coating in a film forming process of the biaxially-oriented film may be employed.

It is preferable that the in-line coat is performed before performing a heat setting of the film. The heat setting is to crystallize a film by heat processing as keeping a stretched film at a temperature that is higher than the stretching temperature and is lower than the melting point of the film. It is preferable that the coating is performed with unstretched film. Alternatively a film is preferably coated right after uniaxially-oriented in longitudinal or lateral direction or right after biaxially-oriented. It is more preferable that the coating is performed right after uniaxially-oriented and then the film is further stretched along at least one axis and is subject to the heat setting. The coat layer can be dried by a drying method such as heat roll contact method, heat medium (air, oil or the like) contact method, infrared heating method and microwave heating method.

It is preferable that the coat layer is formed on the substrate film coated with components dispersed in a solvent by the off-line coat method, such as gravure coat, a reverse coat, a spray coat, kiss coat, comma coat, die coat, knife coat, air knife coat and metaling bar coat, so that a thin layer coating is performed at a high speed. It is preferable that before the coating the substrate film is subject to an adhesion-promotion processing such as a corona discharge processing in an atomosphere of air, nitrogen gas, mixed gas of nitrogen/carbon dioxide or the like, a plasma processing under a reduced pressure, a flame processing and a ultraviolet processing. It is possible that the substrate film is treated with an anchor treatment agent such as urethane resin, epoxy resin and polyethyleneimine.

It is preferable that the water-soluble resin coat layer is dried at 60° C. to 180° C. in case of the off-line coat or at 80° C. to 250° C. in case of the in-line coat. It is preferable that it is dried for 1 to 60 sec, preferably 3 to 30 sec.

It is preferable that the polylactic acid-based resin coat layer is dried at 60° C. to 110° C. in case of the off-line coat, or 80° C. to 180° C. in case of the in-line coat. It is preferable that it is dried for 1 to 60 sec, preferably 3 to 30 sec.

[Coating Agent Containing Water-Soluble Resin]

It is preferable that a coating agent containing the water-soluble resin is a solution in which components are dissolved uniformly. A solvent is preferably water or a mixed solution of water/lower alcohol. It is more preferable to employ the mixed solution of water/lower alcohol.

From viewpoints of viscosity, drying efficiency and productivity, such as coating property of the coating agent, it is preferable that the coating agent containing the water-soluble resin has a solid content concentration of 1.0 mass % or more and 15 mass % or less. With the coating agent having such a high concentration as more than 15 mass %, the solution viscosity might be too high to control the thickness of the water-soluble resin layer solution. The solvent of the coating agent having such a low concentration as less than 1.0 mass % can be mixed with a low-boiling point solvent having a high affinity to water and high volatility. Alternatively, the coat layer can be dried at a temperature equal to or more than the boiling point of water.

To provide a good coating property, it is possible that the solution contains another water-soluble organic compound as the third component so far as the coating agent containing the water-soluble resin keeps the stability. The water-soluble organic compound may be an alcohol such as methanol, ethanol, n-propanol and isopropanol, a glycol such as ethylene glycol and propylene glycol, a glycol derivative such as methyl cellosolve, ethyl cellosolve and n-butyl cellosolve, a polyol such as glycerin and wax, an ether such as dioxane, an ester such as ethyl acetate, a ketone such as methyl ethyl ketone or the like. From a viewpoint of solution stability, it is preferable that the solution has a pH of 2 to 11.

[Coating Agent Containing Polylactic Acid-Based Resin]

It is preferable that the coating agent containing the polylactic acid-based resin is a solution in which components are dissolved uniformly. It is preferable that the solvent is a single solvent or a mixed solution of two or more kinds of solvents selected from a group consisting of butyl alcohol, chloroform, cyclohexane, acetonitrile, dichloromethane, dichloroethane, ethyl acetate, ethyl ether, dipropyl ether and toluene. From viewpoints of productivity and handling ability, ethyl acetate is particularly preferable.

From viewpoints of viscosity, drying efficiency and productivity, such as coating property of the coating agent, it is preferable that the coating agent containing the polylactic acid-based resin has a solid content concentration of 1.0 mass % or more and 10 mass % or less.

To give a good coating property, it is possible that the solution contains another organic compound as the third component so far as the coating agent containing the polylactic acid-based resin keeps the stability.

[Preparation Method of Coating Agent]

The preparation methods of the coating agent containing the water-soluble resin and the coating agent containing the polylactic acid-based resin are not limited in particular. It is preferable that various additives such as cross-linker and particle are uniformly dispersed with the resin in the coating agent as far as the effect of our invention is not spoiled. It is possible that the solvent is heated with a heater to raise the solubility of the resin as needed. Alternatively, the dispersion may be mechanically forced as applying shear stress with a device, such as homomixer, jet ajiter, ball mill, bead mill, kneader, sand mill and three-roller milling machine.

[Producing Method of Polylactic Acid-Based Resin Film]

The polylactic acid-based resin film comprising a polylactic acid-based resin layer can be produced by the following methods although it is not limited to them.

(1) A method to obtain a polylactic acid-based resin film comprising a polylactic acid-based resin layer, by peeling with hand a layer consisting of the water-soluble resin layer and polylactic acid-based resin layer from the substrate resin and then removing the water-soluble resin layer by dissolving in water solution.

(2) A method to obtain a polylactic acid-based resin film comprising a polylactic acid-based resin layer, by immersing a laminate film provided on the substrate film with the water-soluble resin layer and polylactic acid-based resin layer and then removing the water-soluble resin layer by dissolving in water solution.

The water solution may be various kinds of water solutions such as normal saline and glucose solution, preferably water.

EXAMPLES

<Evaluation Method of Characteristics>

The characteristics are evaluated as follows.

(1) Thickness

The water-soluble resin layer and polylactic acid-based resin layer are laminated to have a height difference on the substrate film to be observed with a confocal laser microscope (VK-9710 made by Keyence Corp.). Then, the membrane thickness is calculated from the height difference. The confocal laser microscope is a measuring device having the following mechanism. Laser beam emitted from the opening of the light source focuses to a sample by an object lens to get fluorescence emitted from the sample. The fluorescence and the laser reflected light are mixed and condensed again by an object lens. The mixed light is separated by a beam splitter to let the laser reflected light pass through so that only the fluorescence is introduced into the sensing device. The fluorescence that has passed through a pinhole is sensed by a light sensing device (photomultiplier tube or avalanche photodiode) so that the light signal is converted into electrical signal to be recorded to a computer. The laser scans a sample at regular intervals to obtain an overall image.

(2) Peeling Ability of Polylactic Acid-Based Resin Layer

The laminate film provided on the substrate film with the water-soluble resin layer and polylactic acid-based resin layer is evaluated into five grades of production easiness of the polylactic acid-based resin film comprising the polylactic acid-based resin layer.

Evaluation Grade 5 (Easily Peeled):

A layer consisting of the water-soluble resin layer and polylactic acid-based resin layer is easily peeled by hand from the substrate film, and then the water-soluble resin layer is dissolved in water (at 23° C.) to obtain a polylactic acid-based resin film.

Evaluation Grade 4 (Peelable):

Evaluation grade 5 is not reached but a layer consisting of the water-soluble resin layer and polylactic acid-based resin layer is easily peeled by hand from the substrate film, and then the water-soluble resin layer is dissolved in water (at 37° C.) to obtain a polylactic acid-based resin film.

Evaluation Grade 3 (Hardly Peeled):

Evaluation grades 5 and 4 are not reached but the laminate film provided with the water-soluble resin layer and polylactic acid-based resin layer on the substrate film is immersed in water (at 23° C.) and then the water-soluble resin layer is dissolved therein and peeled to obtain a polylactic acid-based resin film.

Evaluation Grade 2 (Scarcely Peeled):

Evaluation grades 5, 4 and 3 are not reached but the laminate film provided with the water-soluble resin layer and polylactic acid-based resin layer on the substrate film is immersed in water (at 37° C.) and then the water-soluble resin layer is dissolved therein and peeled to obtain a polylactic acid-based resin film.

Evaluation Grade 1 (not Peeled):

Evaluation grades 5, 4, 3 and 2 are not reached but the laminate film provided with the water-soluble resin layer and polylactic acid-based resin layer on the substrate film is immersed in water and then the water-soluble resin layer is dissolved therein, although the polylactic-acid-based resin layer does not keep a continuous film shape.

(3) Adherence 1

Laminate films evaluated as grades 4 and 5 in the above-described "(2) Peeling ability of polylactic acid-based resin layer" are cut into size of 1 cm×1 cm (1 cm$^2$). The layers consisting of the water-soluble resin layer and polylactic acid-based resin layer are peeled from the substrate film. The polylactic acid-based resin layer sides are placed on the skin of 12 healthy volunteers whose back of hands are sprayed to be wet with water (37° C.). The layers with the water-soluble resin layer are further sprayed with water (37° C.) to remove the water-soluble resin layer, and then naturally dried for 1 hour.

Further, laminate films evaluated as grades 2 and 3 in the above-described "(2) Peeling ability of polylactic acid-based resin layer" are cut into size of 1 cm×1 cm (1 cm$^2$). The layers are immersed in water (37° C.) to remove the water-soluble resin layer to obtain the polylactic acid-resin films, which are placed on 12 healthy volunteers' back of hands and naturally dried for 1 hour.

The dried polylactic acid-based resin layers are visually observed to grade the layers. A layer with no rupture, lift and peeling is graded as "5: Very good". A layer with one of rupture, lift and peeling is graded as "4: Good". A layer with two or more of rupture, lift and peeling is graded as "3: Slightly bad". A layer with all of rupture, lift and peeling is graded as "2: Bad". A layer unable to adhere is graded as "1: Very bad". Such grades are averaged among the 12 healthy volunteers to calculate the average score rounded to the closest whole number.

(4) Adherence 2

The polylactic acid-based resin film prepared by the methods of the grades 2 to 5 in the above-described "(2) Peeling ability of polylactic acid-based resin layer" are cut into discs of 900 mm$^2$ area and immersed with water (10-15° C.) in a petri dish. Then, at temperature of 23±5° C. and relative humidity of 65±20%, the polylactic acid-based film is taken from the water bath to be placed within 30 sec and naturally dried for more than 1 hour in the center part of a commercially available polyurethane resin skin model (BIOSKIN plate made by Beaulax: skin model No. 10C (woman in her 20's): disc shape having diameter 50 mm×thickness 5 mm: hardness level 2: mixing ratio 0.25: black). The hardness level of the skin model is measured under the following condition.

1: Durometer (GS-721N made by TECLOCK Corporation: E type)

2: Constant pressure weighter (GS-710 made by TECLOCK Corporation)

3: Method for measurement (JIS K 6253E)

4: Measurement time (15 sec)

The dried polylactic acid-based resin films are visually observed to grade the films. A film adhering with area of 750 mm$^2$ or more and less than 900 mm$^2$ is graded as "5: Very good". A film adhering with area of 500 mm$^2$ or more and less than 750 mm$^2$ is graded as "4: Good". A film adhering with area of 250 mm$^2$ or more and less than 500 mm$^2$ is graded as "3: Slightly bad". A film adhering with area of 100 mm$^2$ or more and less than 250 mm$^2$ is graded as "2: Bad". A film adhering with area of less than 100 mm$^2$ is graded as "1: Very bad". Such grades are averaged among 10 times of measurement to calculate the average score rounded to the closest whole number.

(5) Center-Line Average Surface Roughness on Substrate Film; SRa Level: Ten-Point Average Surface Roughness; SRz Level Three-dimensional surface roughness on substrate film (SRa and SRz) is measured with a three-dimensional contact probe profilometer ET-30HK (made by Kosaka Laboratory Ltd.). The side to laminate the polylactic acid-based resin layer or water-soluble resin layer is subject to the measurement.

Probe curvature radius: 2 μm
Measured length: 1 mm
Feeding pitch: 5 μm
Measurement times: 81 times
Cutoff level: 0.25 mm
Contact probe load: 10 mg
Speed: 100 μm/s (6) Adhesion to Substrate Film The laminate film is sampled into size of 15 mm in transverse direction (TD) and 10 cm in machine direction (MD). The peeling strength of the substrate film to the polylactic acid-based resin layer or the water-soluble resin layer laminated on the substrate film is measured with a tensile tester (Autograph AG-1S made by Shimadzu Corporation). Before sampling, the film to be measured is pasted on the side opposite to contact side of the substrate film with a cellophane tape ("CELLOTAPE (registered trademark)" made by Nichiban Co., Ltd.; CT-18; substrate: cellophane, adhesive: rubber). The peeling test is performed at peeling speed of 200 m/min and peeling angle of 180 degrees as being contacted on the CELLOTAPE side. The "MD" means a rewind direction in which the substrate film is manufactured as rolled while the "TD" means a direction orthogonal to the "MD". The sampling and the measurement are performed in a room at 27±5° C. and humidity of 65±5% RH.

Less than $5 \times 10^{-3}$ [N/10 mm] "0"

$5 \times 10^{-3}$ or more and less than $100 \times 10^{-3}$ [N/10 mm] "5"

$100 \times 10^{-3}$ or more and less than $300 \times 10^{-3}$ [N/10 mm] "4"

$300 \times 10^{-3}$ or more and less than $1,000 \times 10^{-3}$ [N/10 mm] "3"

$1,000 \times 10^{-3}$ or more and less than $2,000 \times 10^{-3}$ [N/10 mm] "2"

2,000×10⁻³ or more and less than 5,000×10⁻³ [N/10 mm] "1"

5,000×10⁻³ or more [N/10 mm] "0"

The above-described scores are averaged (to be rounded off to the closest whole number) among 10 times of tests.

(7) Pinhole

The polylactic acid-based resin film prepared by the methods of the grades 2 to 5 in the above-described "(2) Peeling ability of polylactic acid-based resin layer" are cut into discs of 900 mm² area and immersed with water (10-15° C.) in a petri dish. Then, at temperature of 23±5° C. and relative humidity of 65±20%, the polylactic acid-based film is taken from the water bath to be placed within 30 sec and naturally dried for more than 1 hour in the center part of a commercially available polyurethane resin skin model (BIOSKIN plate made by Beaulax: skin model No. 10C (woman in her 20's): disc shape having diameter 50 mm×thickness 5 mm: hardness level 2: mixing ratio 0.25: white). A red soakage ("AGELESS seal check" made by Mitsubishi Gas Chemical Company, Inc.) containing azo-based oil-soluble dye is applied with a soaked cotton swab to the surface of the polylactic acid-based resin film. It is left for 3 min and then the red soakage remained on the surface is removed with a cotton swab. The bleeding stains on the skin model are visually observed and counted as a pinhole number.

Less than five pinholes: 5
5 or more and less than 10 pinholes: 4
10 or more and less than 15 pinholes: 3
15 or more and less than 20 pinholes: 2
20 or more pinholes: 1

The above-described scores are averaged (rounded off to the closest whole number) among 10 times of tests.

[Substrate Film]

(PET-1)

Biaxially oriented polyester film ("Lumirror" (registered trademark) made by Toray Industries, Inc.; type: S10; thickness: 100 μm).

(PET-2)

Biaxially oriented polyester film ("Lumirror" (registered trademark) made by Toray Industries, Inc.; type: T60; thickness: 100 μm).

(PET-3)

Biaxially oriented polyester film ("Lumirror" (registered trademark) made by Toray Industries, Inc.; type: X10S; thickness: 50 μm).

[Polylactic Acid-Based Resin]

(PLA-1)

Poly-D-lactic acid of 12 mol %; melting point of 150° C.; poly-L-lactic acid-based resin (4060D made by NatureWorks LLC) of weight average molecular weight of 220,000 in terms of PMMA.

(PLA-2)

Poly-D-lactic acid of 4.8 mol %; melting point of 150° C.; poly-L-lactic acid-based resin (4042D made by NatureWorks LLC) of weight average molecular weight of 220,000 in terms of PMMA.

(PLA-3)

Poly-D-lactic acid of 1.4 mol %; melting point of 150° C.; poly-L-lactic acid-based resin (4032D made by NatureWorks LLC) of weight average molecular weight of 220,000 in terms of PMMA.

[Water-Soluble Resin]

(PVA-1)

Polyvinyl alcohol ("GOHSENOL" EG-05P made by Nippon Synthetic Chemical Industry Co., Ltd.) of saponification degree 88 mol %; viscosity 5 mPa·s (4 mass % water solution; 20° C.).

(PVA-2)

Polyvinyl alcohol (functional polymer KM-118 made by Kuraray Co., Ltd.) of saponification degree 97 mol %; viscosity 30 mPa·s (4 mass % water solution, 20° C.).

(PVA-3)

Polyvinyl alcohol ("GOHSENOL" N-11 made by Nippon Synthetic Chemical Industry Co., Ltd.) of saponification degree 99 mol %; viscosity 15 mPa·s (4 mass % water solution; 20° C.).

(Pullulan-1)

Pullulan (pullulan PI-20 made by Hayashibara Co., Ltd.) of weight average molecular weight 263±59 kilo Daltons, polymerization degree (=weight average molecular weight/number average molecular weight) 23.8; viscosity 100-180 mm²/s (temperature 30° C.; 10 mass % water solution of solid content concentration).

Example 1

Water-soluble resin PVA-1 was dissolved in water with a heating-type homogenizer and mixed with isopropyl alcohol by 20 mass % to prepare a water-soluble resin emulsion liquid, which was applied to a side of substrate film PET-1 by the applicator method to have dry membrane thickness of 15 μm and dried for 10 sec in a hot wind dryer at 90° C. to prepare a laminate film. Further, a solution in which polylactic acid-based resin PLA-1 was dissolved in ethyl acetate was applied to it with a metaling bar to have dry membrane thickness of 10 nm, and was dried for 5 sec in a hot-wind dryer at 70° C. to prepare a laminate film provided with a polylactic acid-based resin layer. Characteristics of thus obtained laminate film are shown in Table 1. As shown in Table 1, the laminate film had a polylactic acid-based resin layer having 5th grade of peeling ability and 5th grade of adherence.

Example 2

A laminate film was prepared by the same method as Example 1, except that the polylactic acid-based resin layer had thickness of 50 nm. Characteristics of thus obtained laminate film are shown in Table 1.

Example 3

A laminate film was prepared by the same method as Example 1, except that the polylactic acid-based resin layer had thickness of 500 nm. Characteristics of thus obtained laminate film are shown in Table 1.

Example 4

A laminate film was prepared by the same method as Example 1, except that the water-soluble resin layer had thickness of 0.1 μm. Characteristics of thus obtained laminate film are shown in Table 1.

Example 5

A laminate film was prepared by the same method as Example 1, except that the water-soluble resin layer had thickness of 0.1 μm and the polylactic acid-based resin layer had thickness of 500 nm. Characteristics of thus obtained laminate film are shown in Table 1.

Example 6

A laminate film was prepared by the same method as Example 1, except that substrate film/polylactic acid-based resin layer/water-soluble resin layer were laminated in this order. Characteristics of thus obtained laminate film are shown in Table 1.

Example 7

A laminate film was prepared by the same method as Example 1, except that the water-soluble resin was PVA-2 while the polylactic acid-based resin layer had thickness of 100 nm. Characteristics of thus obtained laminate film are shown in Table 1.

Example 8

A laminate film was prepared by the same method as Example 1, except that a solution in which polylactic acid-based resin PLA-2 was dissolved in ethyl acetate heated at 90° C. was employed. Characteristics of thus obtained laminate film are shown in Table 1.

Examples 9-11

A laminate film was prepared by the same method as Example 1, except that the polylactic acid-based resin layer and the water-soluble resin layer had thicknesses as shown in Table 2. Characteristics of thus obtained laminate film are shown in Table 2.

Examples 12-14

A laminate film was prepared by the same method as Example 1, except that the substrate film was PET-2 and the polylactic acid-based resin layer and the water-soluble resin layer had thicknesses as shown in Table 2. Characteristics of thus obtained laminate film are shown in Table 2.

Example 15-16

A laminate film was prepared by the same method as Example 1, except that the substrate film was PET-2 and water-soluble resin pullulan-1 was not mixed with isopropyl alcohol to prepare a water soluble resin emulsion while polylactic acid-based resin layer and the water-soluble resin layer had thicknesses as shown in Table 3. Characteristics of thus obtained laminate film are shown in Table 3.

Comparative Example 1

A laminate film was prepared by the same method as Example 1, except that the water-soluble resin layer had thickness of 30 μm. Characteristics of thus obtained laminate film are shown in Table 4.

Comparative Example 2

A laminate film was prepared by the same method as Example 1, except that the polylactic acid-based resin layer had thickness of 5 μm. Characteristics of thus obtained laminate film are shown in Table 4.

Comparative Example 3

A laminate film was prepared by the same method as Example 1, except that the water-soluble resin layer had thickness of 0.05 μm and the polylactic acid-based resin layer had thickness of 500 nm. Characteristics of thus obtained laminate film are shown in Table 4.

Comparative Example 4

A laminate film was prepared by the same method as Example 1, except that the water-soluble resin layer is PVA-3 while the water-soluble resin layer had thickness of 17 μm and the polylactic acid-based resin layer had thickness of 100 nm. Characteristics of thus obtained laminate film are shown in Table 4.

Comparative Example 5

A laminate film provided with the water-soluble resin layer was prepared by the same method as Example 1. Then, the polylactic acid-based resin PLA-3 was not able to dissolve in ethyl acetate heated at 90° C., so that the coating was not performed.

Comparative Example 6

A laminate film was prepared by the same method as Comparative Example 3, except that the substrate film is PET-3. Characteristics of thus obtained laminate film are shown in Table 4.

TABLE 1

| | | Example 1 | Example 2 | Example 3 | Example 4 | Example 5 | Example 6 | Example 7 | Example 8 |
|---|---|---|---|---|---|---|---|---|---|
| Substrate film | Type | PET-1 | PET-1 | PET-1 | PET-1 | PET-1 | PET-1 | PET-1 | PET-1 |
| | SRa [nm] | 30 | 30 | 30 | 30 | 30 | 30 | 30 | 30 |
| | SRz [nm] | 640 | 640 | 640 | 640 | 640 | 640 | 640 | 640 |
| Water-soluble resin layer | Resin type | PVA-1 | PVA-1 | PVA-1 | PVA-1 | PVA-1 | PVA-1 | PVA-2 | PVA-1 |
| | Saponification degree of polyvinyl alcohol [mol %] | 88 | 88 | 88 | 88 | 88 | 88 | 97 | 88 |
| | Thickness after drying [μm] | 15 | 15 | 15 | 0.1 | 0.1 | 15 | 15 | 15 |
| Polylactic acid-based resin layer | Resin type | PLA-1 | PLA-1 | PLA-1 | PLA-1 | PLA-1 | PLA-1 | PLA-1 | PLA-2 |
| | Poly-D-lactic acid [mol %] | 12 | 12 | 12 | 12 | 12 | 12 | 12 | 4.8 |
| | Thickness after drying [nm] | 10 | 50 | 500 | 10 | 500 | 10 | 100 | 10 |

TABLE 1-continued

|  | | Example 1 | Example 2 | Example 3 | Example 4 | Example 5 | Example 6 | Example 7 | Example 8 |
|---|---|---|---|---|---|---|---|---|---|
| Laminating order | — | PET/PVA/PLA | PET/PVA/PLA | PET/PVA/PLA | PET/PVA/PLA | PET/PVA/PLA | PET/PLA/PVA | PET/PVA/PLA | PET/PVA/PLA |
| Peeling ability of polylactic acid-based resin layer | — | 5 | 5 | 5 | 3 | 3 | 5 | 4 | 4 |
| Adherence 1 | — | 5 | 5 | 5 | 3 | 3 | 5 | 4 | 4 |
| Adherence 2 | — | 5 | 5 | 3 | 5 | 3 | 5 | 5 | 5 |
| Adhesion to substrate film | — | 4 | 4 | 4 | 5 | 5 | 3 | 4 | 4 |
| Pinhole | — | 4 | 5 | 5 | 3 | 3 | 4 | 5 | 4 |

TABLE 2

|  |  | Example 9 | Example 10 | Example 11 | Example 12 | Example 13 | Example 14 |
|---|---|---|---|---|---|---|---|
| Substrate film | Type | PET-1 | PET-1 | PET-1 | PET-2 | PET-2 | PET-2 |
|  | SRa [nm] | 30 | 30 | 30 | 15 | 15 | 15 |
|  | SRz [nm] | 640 | 640 | 640 | 370 | 370 | 370 |
| Water-soluble resin layer | Resin type | PVA-1 | PVA-1 | PVA-1 | PVA-1 | PVA-1 | PVA-1 |
|  | Saponification degree of polyvinyl alcohol [mol %] | 88 | 88 | 88 | 88 | 88 | 88 |
|  | Thickness after drying [μm] | 10 | 4 | 4 | 0.1 | 0.1 | 4 |
| Polylactic acid-based resin layer | Resin type | PLA-1 | PLA-1 | PLA-1 | PLA-1 | PLA-1 | PLA-1 |
|  | Poly-D-lactic acid [mol %] | 12 | 12 | 12 | 12 | 12 | 12 |
|  | Thickness after drying [nm] | 160 | 200 | 160 | 10 | 500 | 160 |
| Laminating order | — | PET/PVA/PLA | PET/PVA/PLA | PET/PVA/PLA | PET/PVA/PLA | PET/PVA/PLA | PET/PVA/PLA |
| Peeling ability of polylactic acid-based resin layer | — | 5 | 5 | 5 | 3 | 3 | 5 |
| Adherence 1 | — | 5 | 5 | 5 | 3 | 3 | 5 |
| Adherence 2 | — | 5 | 5 | 5 | 5 | 3 | 5 |
| Adhesion to substrate film | — | 4 | 5 | 5 | 5 | 5 | 5 |
| Pinhole | — | 5 | 5 | 5 | 4 | 4 | 5 |

TABLE 3

|  |  | Example 15 | Example 16 |
|---|---|---|---|
| Substrate film | Type | PET-2 | PET-2 |
|  | SRa [nm] | 15 | 15 |
|  | SRz [nm] | 370 | 370 |
| Water-soluble resin layer | Resin type | Pullulan-1 | Pullulan-1 |
|  | Saponification degree of polyvinyl alcohol [mol %] | 4 | 4 |
|  | Thickness after drying [μm] | PLA-1 | PLA-1 |
| Polylactic acid-based resin layer | Resin type | 12 | 12 |
|  | Poly-D-lactic acid [mol %] | 200 | 160 |
|  | Thickness after drying [nm] | PET/pullulan-1/PLA | PET/pullulan-1/PLA |
| Laminating order | — | 5 | 5 |
| Peeling ability of polylactic acid-based resin layer | — | 5 | 5 |
| Adherence 1 | — | 5 | 5 |
| Adherence 2 | — | 5 | 5 |
| Adhesion to substrate film | — | 5 | 5 |
| Pinhole | — | 5 | 5 |

TABLE 4

|  |  | Comparative Example 1 | Comparative Example 2 | Comparative Example 3 | Comparative Example 4 | Comparative Example 5 | Comparative Example 6 |
|---|---|---|---|---|---|---|---|
| Substrate film | Type | PET-1 | PET-1 | PET-1 | PET-1 | PET-1 | PET-3 |
|  | SRa [nm] | 30 | 30 | 30 | 30 | 30 | 72 |
|  | SRz [nm] | 640 | 640 | 640 | 640 | 640 | 1,088 |
| Water-soluble resin layer | Resin type | PVA-1 | PVA-1 | PVA-1 | PVA-3 | PVA-1 | PVA-1 |
|  | Saponification degree of | 88 | 88 | 88 | 99 | 88 | 88 |

TABLE 4-continued

|  |  | Comparative Example 1 | Comparative Example 2 | Comparative Example 3 | Comparative Example 4 | Comparative Example 5 | Comparative Example 6 |
|---|---|---|---|---|---|---|---|
|  | polyvinyl alcohol [mol %] |  |  |  |  |  |  |
|  | Thickness after drying [μm] | 30 | 15 | 0.05 | 17 | 15 | 0.05 |
| Polylactic acid-based resin layer | Resin type | PLA-1 | PLA-1 | PLA-1 | PLA-1 | PLA-3 | PLA-1 |
|  | Poly-D-lactic acid [mol %] | 12 | 12 | 12 | 12 | 1.4 | 12 |
|  | Thickness after drying [nm] | 10 | 5 | 500 | 100 | — | 500 |
| Laminating order |  | — | PET/PVA/PLA | PET/PVA/PLA | PET/PVA/PLA | PET/PVA/PLA | — | PET/PVA/PLA |
| Peeling ability of polylactic acid-based resin layer |  | — | 4 | 5 | 5 | 4 | — | 5 |
| Adherence 1 |  | — | 4 | 5 | 5 | 4 | — | 5 |
| Adherence 2 |  | — | 5 | 3 | 4 | 4 | — | 4 |
| Adhesion to substrate film |  | — | 0 | 4 | 5 | 4 | — | 5 |
| Pinhole |  | — | 3 | 2 | 2 | 2 | — | 1 |

INDUSTRIAL APPLICATIONS OF THE INVENTION

Our invention provides a laminate film of which the water-soluble resin layer and the polylactic acid-based resin layer are easily separated from the substrate film. The laminate film comprising the water-soluble resin layer and the polylactic acid-based resin layer is excellent in covering ability, adherence and followability to a soft and curved adherend, as well as compatibility to skin and organs such as viscera, so as to be suitable for a skin external agent such as wound dressing, adhesion prevention material and skin-care product.

The invention claimed is:

1. A laminate film comprising a water-soluble resin layer and a polylactic acid-based resin layer laminated on a polyester or polyolefin substrate film surface, wherein
the water-soluble resin layer has a thickness of 0.1 to 15 μm,
the polylactic acid-based resin layer has a thickness of 10 to 500 nm, and
the substrate film surface has a center-line average surface roughness (SRa) of 3 to 50 nm and a ten-point average surface roughness (SRz) of 50 to 1000 nm.

2. The laminate film according to claim 1, wherein the water-soluble resin layer contains a polyvinyl alcohol.

3. The laminated film according to claim 2, wherein the polyvinyl alcohol has a saponification degree of 85 to 98.5 mol %.

4. The laminate film according to claim 1, wherein the polylactic acid-based resin layer contains a polylactic acid-based resin including a poly-D-lactic acid of 4 to 13 mol %.

5. The laminate film according to claim 1, wherein the water-soluble resin layer contains a pullulan.

* * * * *